(12) United States Patent
Caneppele et al.

(10) Patent No.: US 10,016,310 B2
(45) Date of Patent: *Jul. 10, 2018

(54) WOUND DRESSING ASSEMBLY

(71) Applicant: JOHNSON & JOHNSON CONSUMER INC., Skillman, NJ (US)

(72) Inventors: Leonardo Caneppele, Jacareí-SP (BR); Guaraci Nakamura Rodrigues Conceição, São José dos Campos-SP (BR); Michael W. Eknoian, Warren, NJ (US); Carlos da Silva Macedo, Jr., São José dos Campos-SP (BR); André Narcizo, São José dos Campos-SP (BR); Paulo Cesar de Godoy Oriani, Itatiba-SP (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 867 days.

This patent is subject to a terminal disclaimer.

(21) Appl. No.: 14/448,139

(22) Filed: Jul. 31, 2014

(65) Prior Publication Data
US 2016/0030249 A1    Feb. 4, 2016

(51) Int. Cl.
*A61F 13/00*    (2006.01)
*A61F 13/02*    (2006.01)

(52) U.S. Cl.
CPC ...... *A61F 13/0253* (2013.01); *A61F 13/0008* (2013.01); *A61F 13/00085* (2013.01); *A61F 13/024* (2013.01); *A61F 13/0213* (2013.01); *A61F 13/0226* (2013.01); *A61F 13/0259* (2013.01)

(58) Field of Classification Search
CPC .............. A61F 13/0253; A61F 13/0008; A61F 13/0209; A61F 13/0213; A61F 13/0226
USPC .......................................... 602/189; D24/189
See application file for complete search history.

(56) References Cited

U.S. PATENT DOCUMENTS

| 3,521,631 A | 7/1970 | Gardner et al. |
| 3,885,559 A | 5/1975 | Economou |

(Continued)

FOREIGN PATENT DOCUMENTS

| GB | 2197590 A | 5/1988 |
| WO | WO 1994/012134 A | 6/1994 |

(Continued)

*Primary Examiner* — Kim M Lewis

(57) ABSTRACT

A wound dressing assembly includes a wound cover and a carrier. The wound cover has a length and width substantially greater than a height (or thickness), a first major surface, and a second major surface, opposite the first. The first major surface has disposed thereon a wound cover pressure sensitive adhesive comprising a colloidal absorbent, and it is arranged and configured to adhere to mammalian skin during use. The carrier has a length and width substantially greater than a height (or thickness), a first major surface, and a second major surface, opposite the first. The first major surface of the carrier is disposed in facing relation and is removably attached to the second major surface of the wound cover, and it has disposed thereon at least one pressure sensitive adhesive. After application of the wound cover to skin for use, the carrier is removable from the wound cover to leave the wound cover adhered to the skin.

1 Claim, 3 Drawing Sheets

(56) References Cited

U.S. PATENT DOCUMENTS

| | | | |
|---|---|---|---|
| 3,888,247 A * | 6/1975 | Stenvall | A61F 13/0203 602/52 |
| 4,598,004 A | 7/1986 | Heinecke | |
| 4,638,796 A | 1/1987 | Sims | |
| 5,000,172 A * | 3/1991 | Ward | A61F 13/023 128/888 |
| 5,086,764 A * | 2/1992 | Gilman | A61F 13/0203 128/888 |
| 5,112,618 A | 5/1992 | Cartmell | |
| 5,465,735 A * | 11/1995 | Patel | A61F 13/022 128/888 |
| 5,501,661 A * | 3/1996 | Cartmell | A61F 13/023 424/443 |
| 5,685,833 A * | 11/1997 | Turngren | A61F 13/0276 206/441 |
| 5,780,048 A | 7/1998 | Lee | |
| 5,891,077 A * | 4/1999 | Gilman | A61F 13/025 602/44 |
| 6,043,408 A | 3/2000 | Geng | |
| 6,093,465 A * | 7/2000 | Gilchrist | A61F 13/023 428/138 |
| 6,124,521 A | 9/2000 | Roberts | |
| 6,255,552 B1 | 7/2001 | Cummings et al. | |
| 8,697,932 B2 * | 4/2014 | Tunius | A61L 15/585 522/174 |
| 2004/0162512 A1 * | 8/2004 | Liedtke | A61F 13/0203 602/59 |
| 2005/0101899 A1 | 5/2005 | Wegmann | |
| 2008/0051688 A1 | 2/2008 | Lowe | |
| 2008/0091133 A1 * | 4/2008 | Matter | A61M 1/0058 602/41 |
| 2011/0015557 A1 * | 1/2011 | Aali | A61F 13/00068 602/56 |
| 2011/0130699 A1 * | 6/2011 | Madsen | A61F 13/023 602/57 |
| 2012/0029405 A1 * | 2/2012 | Cataldi | A61F 13/00063 602/48 |
| 2012/0037656 A1 | 2/2012 | Rattner et al. | |
| 2012/0323105 A1 | 12/2012 | Sonnenborg et al. | |
| 2014/0128790 A1 | 5/2014 | Nokes | |

FOREIGN PATENT DOCUMENTS

| | | |
|---|---|---|
| WO | WO 2008/019310 A1 | 2/2008 |
| WO | WO 2009/110836 A1 | 9/2009 |
| WO | WO 2013/156034 A1 | 10/2013 |

* cited by examiner

WOUND DRESSING ASSEMBLY

FIELD OF THE INVENTION

The present invention relates to wound dressings for use on the skin. More specifically, the invention is a wound dressing with a removable component.

BACKGROUND OF THE INVENTION

Adhesive articles such as tapes and wound dressings and bandages are well known in the art and are used for various medical applications for humans and other mammals and for sports protection of humans. In the case of wound dressing, a sterile wound covering element, such as a pad, contacts the wound, and a backing layer, or carrier, coated with a pressure sensitive adhesive provides secure attachment of the dressing to bare skin adjacent to a wound.

Wound dressings such as bandages are typically constructed so that the wound-covering element and the backing layer are securely attached to one another. When the user desires to remove the dressing, such as to change the dressing, the wound covering element and the backing layer are pulled off the user's skin simultaneously. This leaves the wound exposed and unprotected from the surrounding environment. Other times, such as for cosmetic reasons, or after an initial healing period, a user may desire less restrictive and/or cumbersome protection may be desired. Thus, the user may desire to remove only a backing/cushioning portion, leaving the wound covering element in contact with the wound.

Alternatively, some wound dressings are very flexible or difficult to handle without wrinkling or adhering to themselves. Thus, wound dressing applicators made of wound dressing elements and applicator elements are used. In these cases, the dressing/applicator system is disposed on the user's skin at the wound site. Then, the applicator element is removed, leaving the dressing at the wound site. In these systems, the bandage elements, the wound covering element and the backing layer are securely attached to one another. Examples of such systems include Sonnenborg et al., US Patent App. No 2012/0323105, and Smith & Nephew PLC, WO Patent App. No. 94/12134.

Other systems deliver an adhesive wound closure to the skin, but the closure lacks absorbent capacity to take up any wound exudates. Thus, additional exudate-absorbing pads are required until seepage ends, or such exudates may pool between the wound and the closure. Examples of such systems include:

Stenvall, U.S. Pat. No. 3,888,247, purports to disclose a first aid bandage having a flexible, adhesive-coated backing having an absorbent pad secured thereto and a strip of microporous breathable surgical tape superposed over the absorbent pad. Thus, upon application of the first aid bandage the entirety of the skin-facing surface of the bandage is adhesive, and in use, a wound is covered by the adhesive layer of the surgical tape and the surgical tape is at least partially covered by the absorbent pad of the bandage. Finally, the flexible, adhesive-coated backing layer protects the entirety of the bandage. After sufficient time has elapsed to allow for cessation of bleeding and for clotting to occur, backing layer and pad can be removed leaving the smaller strip of microporous breathable surgical tape covering the wound. This may leave a blood-stained surgical tape at the wound site.

Lee, U.S. Pat. No. 5,780,048, purports to disclose a first aid bandage dressing system incorporating a cyanoacrylate wound binding layer that is stored in an air-tight or vacuum package prior to use. The cyanoacrylate wound binding layer is described as occlusive and adhesive without the need for additional tape to hold it in place once it is cured by exposure to the moisture and oxygen in air. There is no absorbent capacity disclosed to accommodate wound exudate, which may pool below the wound binding layer, if inadequately applied.

Lowe, US Patent Appn. No. 2008/0051688 A1, purports to disclose a two layered wound dressing having a bottom layer pierced with a series of apertures for adhesive attachment to the skin and a top layer has a very low moisture vapor transmission rate to close the wound from then environment and to keep moisture near the skin to promote healing. After initial healing, the top layer is removed and the apertures permit a near 100% moisture vapor and oxygen transmission between the skin and the environment. Again, there is no absorbent capacity disclosed in this system, and blood or other wound exudates may pool in the regions of the apertures in the bottom layer.

Each of these wound closure systems lacks absorbent capacity and may result in blood-stained dressings. Therefore, a need exists for a wound dressing assembly that incorporates both wound closure adhesive properties and sufficient exudate absorbing capacity that can effectively protect healing wounds. In addition, the above solutions have failed to completely solve the issue of removal of only the carrier, leaving the wound covering element in contact with the wound, protecting the wound from the surrounding environment.

SUMMARY OF THE INVENTION

Surprisingly, we have found a novel way to provide a wound dressing assembly that incorporates both wound closure adhesive properties and sufficient exudate absorbing capacity that can effectively protect wounds as they heal.

In one aspect of the invention, a wound dressing assembly includes a wound cover and a carrier. The wound cover has a length and width substantially greater than a height (or thickness), a first major surface, and a second major surface, opposite the first. The first major surface has disposed thereon a wound cover pressure sensitive adhesive comprising a colloidal absorbent, and it is arranged and configured to adhere to mammalian skin during use. The carrier has a length and width substantially greater than a height (or thickness), a first major surface, and a second major surface, opposite the first. The first major surface of the carrier is disposed in facing relation and is removably attached to the second major surface of the wound cover, and it has disposed thereon at least one pressure sensitive adhesive. After application of the wound cover to skin for use, the carrier is removable from the wound cover to leave the wound cover adhered to the skin.

In another aspect of the invention, the above wound dressing assembly is applied to the mammalian skin and left on the skin for a desired period of time. Subsequently, the carrier is removed from the wound cover, leaving the wound cover adhered to the mammalian skin.

BRIEF DESCRIPTION OF THE DRAWINGS

An embodiment of this invention will now be described in greater detail, by way of illustration only, with reference to the accompanying drawings, in which.

DETAILED DESCRIPTION OF THE INVENTION

Again, wound dressings are typically constructed so that the wound covering element and the backing layer, or carrier, are securely attached to one another. When the dressing is removed, the wound covering element and the backing layer are pulled off the user's skin simultaneously, leaving the wound exposed and unprotected from the surrounding environment. If, for cosmetic reasons or after an initial healing period, the user desires to remove the backing layer, leaving the wound covering element in contact with the wound, current dressings cannot be employed. Therefore, we have provided novel wound dressings in which the carriers are easily removable from mammalian skin leaving the wound cover on the skin.

As used herein the specification and the claims, the term "release liner" and variants thereof relate to a web of material that has at least one surface arranged and configured to be removable from a pressure sensitive adhesive surface in contact therewith. Generally, a release liner is used to isolate the pressure sensitive adhesive from the environment to retain the surface tack thereof prior to use. The release liner is removed to expose the pressure sensitive adhesive for use.

As used herein the specification and the claims, the term "release agent" and variants thereof relate to a coating or other surface treatment to enhance the removal of the surface from a pressure sensitive adhesive surface in contact therewith.

Figure 1:
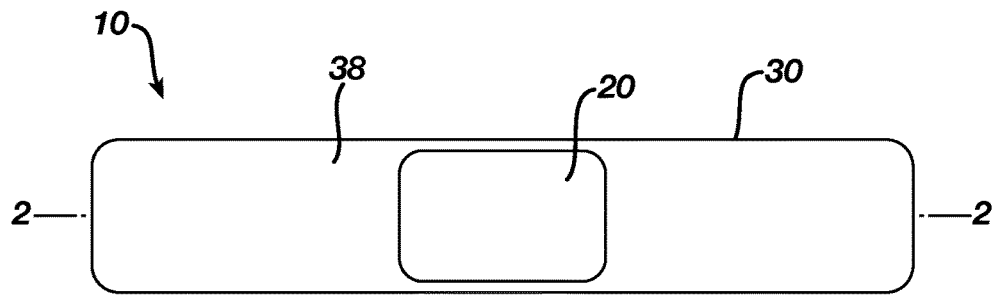
FIG. 1 is a top plan view of a first embodiment of a wound dressing assembly of the present invention.
Figure 2:
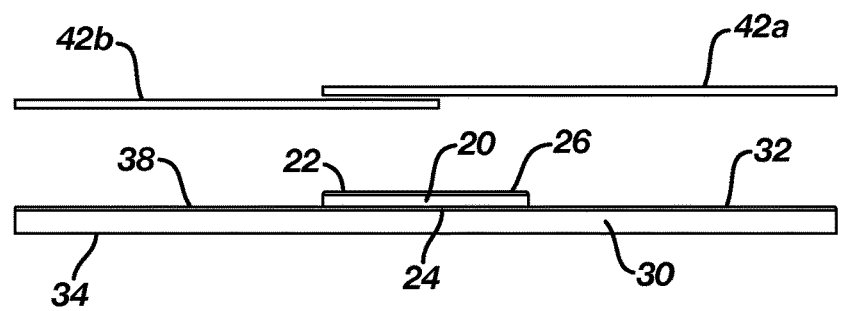
FIG. 2 is a cross-sectional view of the wound dressing assembly of FIG. 1 taken along the 2-2 plane.

FIGS. 1 and 2 illustrate a first embodiment of a wound dressing assembly of the present invention. The wound dressing assembly 10, which may also be referred to as an adhesive bandage or a sticking plaster, comprises a wound cover 20 and a carrier 30.

Wound cover 20 has a length and width substantially greater than its height, and has a first major surface 22 and a second major surface 24 opposite first major surface 22. First major surface 22 has disposed thereon a wound cover pressure sensitive adhesive 26 arranged and configured to adhere to mammalian skin during use.

Carrier 30 has a length and width substantially greater than its height, and has a first major surface 32 and a second major surface 34 opposite first major surface 32. First major surface 32 has disposed thereon at least one pressure sensitive adhesive 38 arranged and configured to adhere to mammalian skin during use.

First major surface 22 of wound cover 20 faces the application site of wound dressing assembly 10, while the second major surface 24 of wound cover 20 faces away from the application site. Likewise, first major surface 32 of carrier 30 faces the application site of wound dressing assembly 10, while the second major surface 34 of carrier 30 faces away from the application site.

First major surface 32 of carrier 30 is in facing relationship and removably attached to second major surface 24 of wound cover 20.

In some embodiments of wound dressing assembly 10, wound cover 20 and carrier 30 are substantially coextensive. In other embodiments, such as that illustrated in FIGS. 1 and 2, carrier 30 superposes and extends beyond at least a portion of wound cover 20.

Though optional, wound dressing assembly 10 may also have release liners, such as 42a and 42b in one embodiment, applied to wound cover pressure sensitive adhesive 26 and carrier pressure sensitive adhesive 38. Release liners 42a and 42b are removed from wound dressing assembly 10 prior to application by the user.

Wound cover 20 has several functions. It serves as a barrier between wound cover pressure sensitive adhesive 26 and pressure sensitive adhesive 38. Wound cover 20 also protects the wound site once, as described below, carrier 30 is removed from the wound site by the user.

Wound cover 20 is thin, highly flexible or deformable, water-impervious, or substantially impervious to bodily fluids, yet breathable. In some embodiments, second major surface 24 of wound cover 20 is water-impervious, or substantially impervious to bodily fluids. In general, the thickness of wound cover 20 is between about 80 to about 300 microns ("μm"), preferably between about 100 to about 200 μm and most preferably, about 150 μm to achieve the forming and flexing characteristics desired.

Preferably, the materials used in wound cover 20 are conformable to the contours of the body, and flexible so as to permit free movement of the body part wearing wound dressing assembly 10. Wound cover 20 is very lightweight, and may be elastic (elastomeric) in character. It can be a woven or nonwoven fabric, a film, or a foam. Preferred polymeric materials useful in forming the wound cover 20 could include polyolefin (such as polyethylene), polyurethane, and polyvinylchloride. Other examples of backings include, but are not limited to, nonwoven, woven, or knitted fabrics such as cotton, polyester, polyurethane, rayon and the like.

A polyethylene film may be used as wound cover 20. However, particularly effective results can be achieved with stretchable, elastomeric films formed of polyurethane, which has the further advantage of gas (including water vapor) transmissibility. Preferred films have a Moisture Vapor Transmission Rate (MVTR) of greater than about 300 g/m$^2$/24 h (ASTM D6701 (2001), which can be measured using a Mocon PERMETRAN-W MODEL 101K testing device. It is to be understood, however, that other flexible, water insoluble polymeric films known in the art may be used. In addition, in some applications, dissolvable films can be used. Furthermore, wound cover 20 may be formed from closed-cell polymeric foam, particularly one with an integral skin covering the side facing away from the skin of the user. Foam layers formed of polyurethane or polyethylenes are suitable, while other polymeric foams having similar properties may be used. In addition, wound cover 20 may be made from other polyolefins, vinyl polyethylene acetate, textile non-woven fabrics, rubber, tissue paper, plastic netting, adsorbent pads or other materials known in the adhesive article art. One such material is plastic netting sold under the trade name DELNET® (Delstar Technologies, Middletown, Del.).

In a preferred embodiment, wound cover 20 is substantially transparent. This may be particularly desirable to protect small wounds, such as non-bleeding cuts and the like, without visible bandages. In other embodiments, wound cover 20 is substantially translucent. In still other embodiments, wound cover 20 is substantially opaque. An opaque wound cover 20 can serve to hide the wound from view once carrier 30 is removed from the user's skin. In other embodiments, such as for use in children's wound dressing assemblies 10, second major surface 24 of wound cover 20 may be decorated. Decorations include color or colors, decals, printed messages, or cartoons. The decoration serves the dual purpose of hiding the wound site from view, as well as providing entertainment for the wearer of the wound dressing assembly 10.

Again, first major surface 22 of wound cover 20 has disposed thereon a wound cover pressure sensitive adhesive 26 arranged and configured to adhere to mammalian skin during use. Adhesive 26 comprises at least one colloidal absorbent component dispersed therein. The colloidal absorbent component used may be any substance that has a good performance in this utilization. Preferred colloidal absorbent components include hydrocolloids, such as, sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof, among others.

Hydrocolloids, such as sodium carboxymethylcellulose and pectin, among others, are agents that form gels as soon as they come into contact with the bodily fluids from the wound. When used in adhesive bandages, these hydrocolloids are combined with elastomers and/or adhesives. Preferably, the wound cover provides a humid environment but without saturation, cicatrisation, which is a situation suitable for acceleration of the healing.

Adhesive 26 may be any conventional adhesive known for such use, as for example pressure acrylic adhesives, among others. Additionally, such an adhesive may contain a resin for increasing adhesion, a cohesion increasing agent, an absorption agent (preferably a polyacrylate superabsorbent, a polyacrylate salt superabsorbent or a mixture thereof), a plasticizer and optionally a pigment. Adhesive 26 may further be configured in discontinuous patterns, arranged in lines, screen, spray or any other which a person skilled in the art understands as discontinuous, composed by an elastomeric base.

Again, first major surface 22 of wound cover 20 has disposed thereon a wound cover pressure sensitive adhesive 26, and first major surface 32 of carrier 30 has disposed thereon at least one pressure sensitive adhesive 38. Wound cover pressure sensitive adhesive 26 has an adhesion to first major surface 22 of wound cover 20, and an adhesion to mammalian skin. The relative adhesion of the different pressure sensitive adhesives can be determined by applying to a user's skin or a test skin sample and removing the carrier from the skin/wound cover. Thus, pressure sensitive adhesive 38 disposed on the first major surface 32 of carrier 30 has an adhesion to second major surface 24 of wound cover 20 that is less than the adhesion of the wound cover pressure sensitive adhesive 26 to the user's skin.

While the adhesive of the wound cover and the carrier may be the same or similar (with appropriate release agent treatment of the second major surface of the wound cover), it is preferred that the wound cover pressure sensitive adhesive is a hydrocolloid adhesive—an adhesive matrix that incorporates comprises hydrocolloids or hydrogels as described above. This permits the wound cover to avoid known fibrous absorbent structures and can be substantially transparent while providing sufficient absorbent capacity to accept minor levels of wound exudate.

The release agent treatment of the second major surface of the wound cover permits the easy removal of the carrier from the skin and wound cover to retain protection of the wound site while removing the carrier. One of ordinary skill in the art will recognize appropriate release agents, including without limitation, coatings such as silicone-based (including siloxane) coatings, polyvinyl octadecyl carbonate-based coatings (PVODC), and other surface treatments.

Carrier 30 may have various shapes, including but not limited to, rectangular, oval, ovoid, or oblong. The shape of wound dressing assembly 10 is defined by the shape of carrier 30. Carrier 30 may be thin, highly flexible or deformable, and may be water-impervious or substantially impervious to bodily fluids. In general, the thickness of carrier 30 is between about 50 to about 500 µm to achieve the forming and flexing characteristics desired. The carrier will be thicker (e.g., about 200 to about 500 µm) if more substantial wound cushioning is desired, while a thinner carrier generally will be more flexible.

It is desired for the material used in carrier 30 to be both conformable to the contours of the body, and flexible so as to permit free movement of the body part wearing the product. Further, carrier 30 could be lightweight, and may be elastic (elastomeric) in character. It can be a woven or nonwoven fabric, a film or a foam. Polymeric materials useful in forming the carrier 30 include polyolefin (such as polyethylene), polyurethane, and polyvinylchloride. Other examples of backings include, but are not limited to, nonwoven, woven, or knitted fabrics such as cotton, polyester, polyurethane, rayon and the like.

A polyethylene film may be used as carrier 30, and particularly effective results can be achieved with stretchable, elastomeric films formed of polyurethane, which has the further advantage of gas (including water vapor) transmissibility. It is to be understood, however, that other flexible, water insoluble polymeric films known in the art may be used. Furthermore, carrier 30 may be formed from closed-cell polymeric foam, particularly one with an integral skin covering the side facing away from the skin of the user. Foam layers formed of polyurethane or polyethylenes are suitable, while other polymeric foams having similar properties may be used. In addition, carrier 30 may be made from other polyolefins, vinyl polyethylene acetate, textile nonwoven fabrics, rubber, or other materials known in the adhesive article art. Polymers used to make carrier 30 used in bandages of the present invention may exhibit viscosity of about 500 to 500,000 centipoises at temperatures of about 190° C., or about 1,000 to 30,000 centipoises at temperatures of about 190° C., or about 3,000 to 15,000 centipoises at temperatures of about 190° C. Carrier 30 may be impermeable to liquid, but permeable to gas, which allows the wound and the skin to which the elongate wound dressing assembly 10 of the present invention is adhered to breathe. In one embodiment, carrier 30 may have pores of such a size that will allow only the passage of gases, which have molecules of extremely small size. Finally, one can conceive of a backing layer that is perforated for more ventilation of the skin. Perforations may be circular in area and have a range of diameters, such as from about 0.1 to about 0.8 millimeters. However, carrier 30 may be totally impermeable to gases, when necessary.

The dimensions of carrier 30 will depend on the proposed use of wound dressing assembly 10. Typically, small wounds use dressings which are about 15 mm in their smallest dimension. Large wounds typically use dressings which are about 100 mm in their largest dimension.

In some embodiments, carrier 30 is substantially transparent. In other embodiments, carrier 30 is substantially translucent. In still other embodiments, carrier 30 is substantially opaque. In yet still other embodiments, such as for use in children's wound dressing assemblies 10, second major surface 34 of carrier 30 may be decorated. Decorations include color or colors, decals, printed messages or cartoons. The decoration serves the dual purpose of hiding the wound site from view, as well as providing entertainment for the wearer of wound dressing assembly 10.

First major surface 32 of carrier 30 has disposed thereon at least one pressure sensitive adhesive 38 arranged and configured to adhere to mammalian skin during use. In general, any of a variety of pressure-sensitive adhesives can be utilized as adhesive 38. In particular, pressure-sensitive adhesives that are biocompatible with human skin are typically utilized. In some embodiments, an adhesive of the present invention may also be either generally water soluble or generally insoluble, or dispersible in an aqueous environment. For instance, commercially available dispersible pressure-sensitive adhesive is sold under the trade name of HL-9415-X and is available from H.B. Fuller Company. Another suitable adhesive includes about 10-75% by weight of a polyalkyloxazoline polymer, 10-75% by weight of a functional diluent comprising a hydroxy compound or a carboxylic acid compound, and 5-50% by weight of a tackifier.

Adhesive 38 may comprise hydrocolloids. The hydrocolloid element used may be any substance that has a good performance in this utilization, as for example, sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof, among others.

Hydrocolloids, such as sodium carboxymethylcellulose and pectin, among others, are agents that form gels as soon as they come into contact with the bodily fluids from the wound. When used in adhesive bandages, these hydrocolloids are combined with elastomers and/or adhesives. Preferably, the adhesive bandage should provide a humid environment but without saturation, cicatrisation, which is a situation suitable for acceleration of the healing.

Adhesive 38 may be any conventional adhesive known for such use, as for example pressure acrylic adhesives, among others. Additionally, such an adhesive may contain a resin for increasing adhesion, a cohesion increasing agent, an absorption agent (preferably a polyacrylate superabsorbent, a polyacrylate salt superabsorbent or a mixture thereof), a plasticizer and optionally a pigment. Adhesive 38 may further be configured in discontinuous patterns, arranged in lines, screen, spray or any other which a person skilled in the art understands as discontinuous, composed by an elastomeric base.

In addition, first major surface 32 of carrier 30 is in facing relationship and removably attached to second major surface 24 of wound cover 20.

Wound dressing assembly 10 is configured so that after application of wound cover 20 to the skin of the user, carrier 30 is removable from wound cover 20 to leave wound cover 20 adhered to mammalian skin. For this to be possible, the adhesion of pressure sensitive adhesive 38 to second major surface 24 of wound cover 20 must be less than the adhesion of wound cover pressure sensitive adhesive 26 to both second major surface 24 of wound cover 20 and to mammalian skin. The result is that carrier 30 is capable of removal from wound cover 20 and mammalian skin while wound cover 20 remains adhered to mammalian skin.

Figure 3:
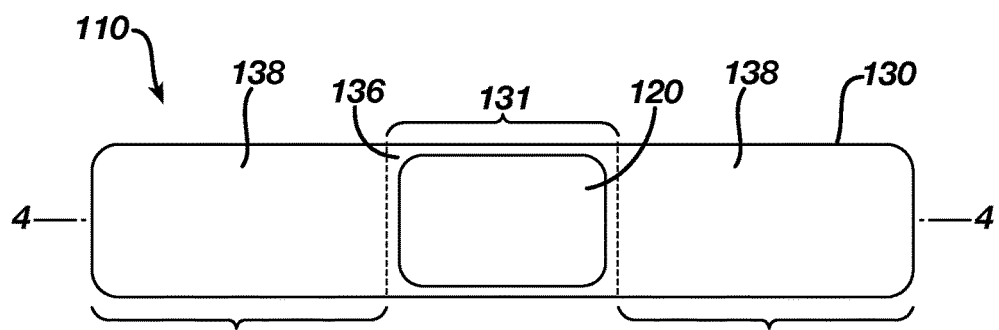
FIG. 3 is a top plan view of a second embodiment of a wound dressing assembly of the present invention.
Figure 4:
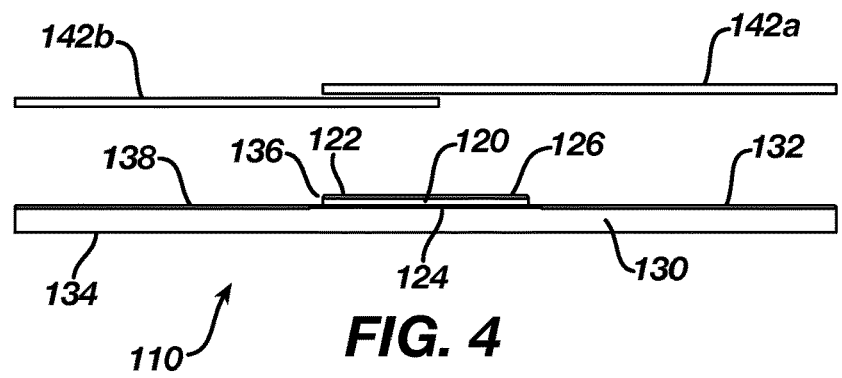
FIG. 4 is a cross-sectional view of the wound dressing assembly of FIG. 3 taken along the 4-4 plane.

FIGS. 3 and 4 illustrate a second embodiment of a wound dressing assembly of the present invention. The wound dressing assembly 110 comprises a wound cover 120 and a carrier 130.

As in the embodiment of FIGS. 1 and 2, wound cover 120 has a length and width substantially greater than its height, and has a first major surface 122 and a second major surface 124 opposite first major surface 122. First major surface 122 has disposed thereon a wound cover pressure sensitive adhesive 126 arranged and configured to adhere to mammalian skin during use.

Carrier 130 has a length and width substantially greater than its height, and has a first major surface 132 and a second major surface 134 opposite first major surface 132. First major surface 132 of carrier 130 has a plurality of zones, a first zone 131 which disposed thereon is a first zone pressure sensitive adhesive 136, and a second zone 133 which disposed thereon is a second zone pressure sensitive adhesive 138 arranged and configured to adhere to mammalian skin during use. First zone 131 may be coextensive with wound cover 120, but it may be substantially coextensive with wound cover 120, or, as shown in FIGS. 3 and 4, larger in area than second major surface 124 of wound cover 120. Second zone 133 at least partially surrounds first zone 131.

First major surface 122 of wound cover 120 faces the application site of wound dressing assembly 110, while the second major surface 124 of wound cover 120 faces away from the application site. Likewise, first major surface 132 of carrier 130 faces the application site of wound dressing assembly 110, while the second major surface 134 of carrier 130 faces away from the application site.

First major surface 132 of carrier 130 is in facing relationship and removably attached to second major surface 124 of wound cover 120.

Though optional, wound dressing assembly 110 may also have release liners, such as 142a and 142b in one embodiment, applied to wound cover pressure sensitive adhesive 126, first zone pressure sensitive adhesive 136, and second zone pressure sensitive adhesive 138. Release liners 142a and 142b are removed from wound dressing assembly 110 prior to application by the user.

As with carrier 30, carrier 130 may have various shapes, may be thin, highly flexible or deformable, can be water-impervious or substantially impervious to bodily fluids, and have thickness between about 0.05 to 0.2 millimeter ("mm") to achieve the forming and flexing characteristics desired. Other characteristics, dimensions, and materials for use in carrier 130 were described above for carrier 30.

Again, second major surface 124 of wound cover 120 is in facing relationship and removably attached to first major surface 132 of carrier 130. Wound cover 120 has several functions. It serves as a barrier between wound cover pressure sensitive adhesive 126 and first zone pressure sensitive adhesive 136. Wound cover 120 also protects the wound site once, as described below, carrier 130 is removed from the wound site by the user. Characteristics, dimensions, and materials for use in wound cover 120 were described above for wound cover 20.

Again, first major surface 122 of wound cover 120 has disposed thereon a wound cover pressure sensitive adhesive 126 arranged and configured to adhere to mammalian skin during use. First major surface 132 of carrier 130 has a first zone 131 which disposed thereon is a first zone pressure sensitive adhesive 136, and a second zone 133 which disposed thereon is a second zone pressure sensitive adhesive 138 arranged and configured to adhere to mammalian skin during use. The characteristics and materials for use in adhesives 126, 136, and 138 were described above for adhesives 26 and 38. First zone pressure sensitive adhesive 138 may be provided by coating the first zone 131 of the carrier 130 with such first zone pressure sensitive adhesive 138, or it may be provided by adhering an intermediate layer having a first zone pressure sensitive adhesive 138 on the surface facing the wound cover 120.

Again, first major surface 122 of wound cover 120 has disposed thereon a wound cover pressure sensitive adhesive 126, and first major surface 132 of carrier 130 has a first zone 131 which disposed thereon is first zone pressure sensitive adhesive 136. Wound cover pressure sensitive adhesive 126 has an adhesion to first major surface 122 of wound cover 120, and an adhesion to mammalian skin. The relative adhesion of the different pressure sensitive adhesives can be determined by applying to a user's skin or a test skin sample and removing the carrier from the skin/wound cover. Thus, first zone pressure sensitive adhesive 136 disposed on first major surface 132 of carrier 130 has an adhesion to second major surface 124 of wound cover 120 that is less than the adhesion of the wound cover pressure sensitive adhesive 26 to the user's skin.

Figure 5:
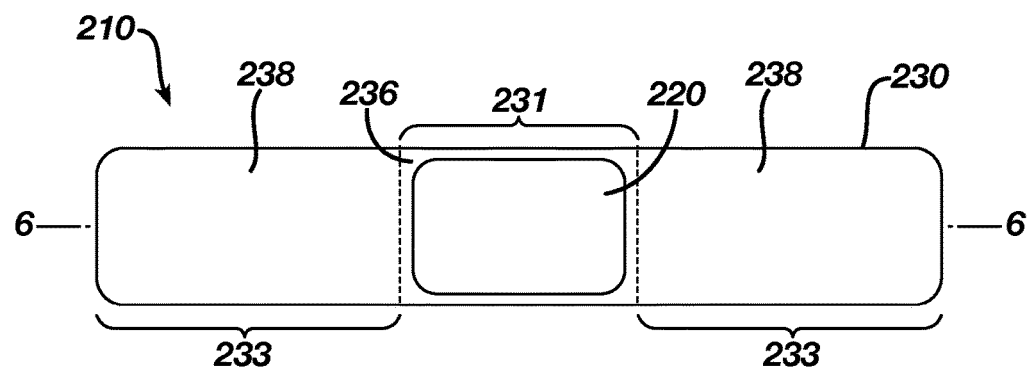
FIG. 5 is a top plan view of a third embodiment of a wound dressing assembly of the present invention.
Figure 6:
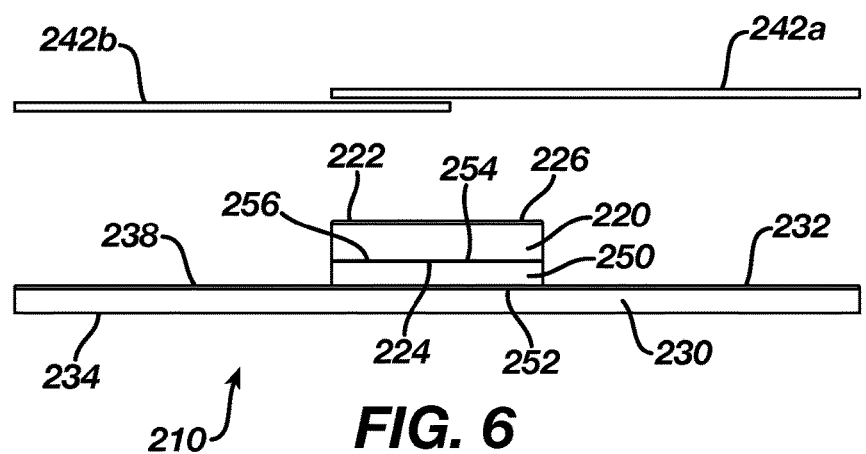
FIG. 6 is a cross-sectional view of the wound dressing assembly of FIG. 5 taken along the 6-6 plane.

FIGS. 5 and 6 illustrate a third embodiment of a wound dressing assembly of the present invention. Wound dressing assembly 210 comprises a wound cover 220, a carrier 230, and a releasable element 250.

Wound cover 220 has a length and width substantially greater than its height, and has a first major surface 222 and a second major surface 224 opposite first major surface 222. First major surface 222 has disposed thereon a wound cover pressure sensitive adhesive 226 arranged and configured to adhere to mammalian skin during use. Second major surface 224 has disposed thereon releasable element 250.

Carrier 230 has a length and width substantially greater than its height, and has a first major surface 232 and a second major surface 234 opposite first major surface 232. First major surface 232 of carrier 230 has disposed thereon at least one pressure sensitive adhesive 238 arranged and configured to adhere to mammalian skin during use.

Releasable element 250 has a length and width substantially greater than its height, and has a first major surface 252 and a second major surface 254 opposite first major surface 252. Second major surface 254 of releasable element 250 has disposed thereon a first zone pressure sensitive adhesive 256. Releasable element 250 is preferably coextensive with wound cover 220 as shown in FIGS. 5 and 6, or may be slightly smaller than wound cover 220.

First major surface 222 of wound cover 220 faces the application site of wound dressing assembly 210, while the second major surface 224 of wound cover 220 faces away from the application site. First major surface 252 of releasable element 250 faces away from the application site, while the second major surface 254 of releasable element 250 faces the application site of wound dressing assembly 210. First major surface 232 of carrier 230 faces the application site of wound dressing assembly 210, while the second major surface 234 of carrier 230 faces away from the application site.

First major surface 232 of carrier 230 is in facing relationship and attached to first major surface 252 of releasable element 250. Second major surface 254 of releasable element 250 is in facing relationship and removably attached to second major surface 224 of wound cover 220.

Though optional, wound dressing assembly 210 may also have release liners, such as 242a and 242b in one embodiment, applied to carrier pressure sensitive adhesive 238 and wound cover pressure sensitive adhesive 226. Release liners 242a and 242b are removed from wound dressing assembly 210 prior to application by the user.

As with carrier 30, carrier 230 may have various shapes, may be thin, highly flexible or deformable, can be water-impervious or substantially impervious to bodily fluids, and have thickness between about 0.05 to 0.2 millimeter ("mm") to achieve the forming and flexing characteristics desired. Other characteristics, dimensions, and materials for use in carrier 230 were described above for carrier 30.

Again, first major surface 232 of carrier 230 is in facing relationship and attached to first major surface 252 of releasable element 250. Releasable element 250 aids in the separation of wound cover 220 from carrier 230 and remains associated with the wound cover 220 after such separation.

Releasable element 250 may be thin, highly flexible or deformable, water-impervious, or substantially impervious to bodily fluids. In general, the thickness of wound cover 20 is as thin as possible to minimally affect the characteristics of the wound cover/releasable element combination left on the skin to maintain the desired forming and flexing characteristics.

It is desired that the material used in releasable element 250 be similar in behavior to the material used in wound cover 220 and carrier 230. The materials must both be conformable to the contours of the body, and flexible so as to permit free movement of the body part wearing wound dressing assembly 210. Releasable element 250 could be lightweight, and may be elastic (elastomeric) in character. It can be a woven or nonwoven fabric, a film, or a foam. Polymeric materials useful in forming releasable element 250 could include polyolefin (such as polyethylene), polyurethane, and polyvinylchloride. Other examples of backings include, but are not limited to, nonwoven, woven, or knitted fabrics such as cotton, polyester, polyurethane, rayon and the like.

A polyethylene film may be used as releasable element 250, and particularly effective results can be achieved with stretchable, elastomeric films formed of polyurethane, which has the further advantage of gas (including water vapor) transmissibility. It is to be understood, however, that other flexible, water insoluble polymeric films known in the art may be used.

Again, second major surface 224 of wound cover 220 is in facing relationship and removably attached to second major surface 254 of releasable element 250. Wound cover 220 protects the wound site once, as described below, carrier 230 is removed from the wound site by the user. Characteristics, dimensions, and materials for use in wound cover 220 were described above for wound cover 20.

Again, first major surface 222 of wound cover 220 has disposed thereon wound cover pressure sensitive adhesive 226 arranged and configured to adhere to mammalian skin during use. Second major surface 254 of releasable element 250 has disposed thereon a first zone pressure sensitive adhesive 256. First major surface 232 of carrier 230 has disposed thereon carrier pressure sensitive adhesive 238 arranged and configured to adhere to mammalian skin during use. The characteristics and materials for use in adhesives 226, 238, and 256 were described above for adhesives 26 and 38.

Again, first major surface 222 of wound cover 220 has disposed thereon a wound cover pressure sensitive adhesive 226, second major surface 254 of releasable element 250 has disposed thereon a first zone pressure sensitive adhesive 256, and first major surface 232 of carrier 230 has disposed thereon carrier pressure sensitive adhesive 238. Wound cover pressure sensitive adhesive 226 has an adhesion to first major surface 222 of wound cover 220, and an adhesion to mammalian skin. The relative adhesion of the different pressure sensitive adhesives can be determined by applying to a user's skin or a test skin sample and removing the carrier from the skin/wound cover. Thus, first zone pressure sensitive adhesive 256 has and adhesion to second major surface 254 of releasable element 250, and an adhesion to second major surface 224 of wound cover 220. Also, carrier pressure sensitive adhesive 238 has an adhesion to first major surface 232 of carrier 230, and an adhesion to first major surface 252 of releasable element 250. The relative adhesion of these layers can be determined as described above. Essentially, the carrier 230 and its related pressure sensitive adhesive should be removable from the releasable element while leaving the wound cover 220 and associated releasable element 250 adhered to the skin.

The difference in adhesion of wound cover 220 to mammalian skin and releasable element 250 to wound cover 220 may be achieved in a number of ways. It can be accomplished by using an adhesive with lesser adhesion in first zone pressure sensitive adhesive 256 than that used in wound cover pressure sensitive adhesive 226. Alternatively, the same adhesives, or adhesives with the same degree of adhesion, may be used in first zone pressure sensitive adhesive 256 and wound cover pressure sensitive adhesive 226. In these embodiments, first zone pressure sensitive adhesive 256 may be configured in discontinuous patterns on second major surface 254 of releasable element 250, with less adhesive applied on second major surface 254 of releasable element 250 than on first major surface 222 of wound cover 220.

Wound dressing assembly 10 is configured so that in use, the article is initially applied by the user to the wound site such that wound cover 20 is disposed on the wound. Then, after a period of time determined by the user, carrier 30 is removed from the wound site, leaving wound cover 20 remaining on the wound site. The period of time from application of wound dressing assembly 10 to the wound site to removal of carrier 30 from the wound site may be greater than about 1 hour, or greater than about 6 hours, or greater than about 12 hours, or greater than about 24 hours, or greater than about 72 hours, for example.

Figure 7:
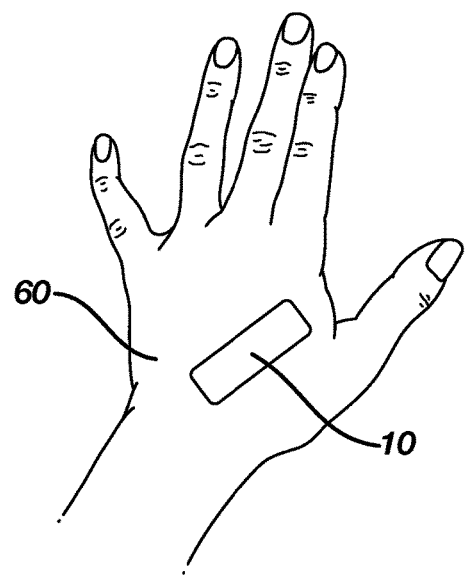
FIG. 7 illustrates a first step of wound dressing assembly use when the assembly is first applied to the hand of a user.
Figure 8:
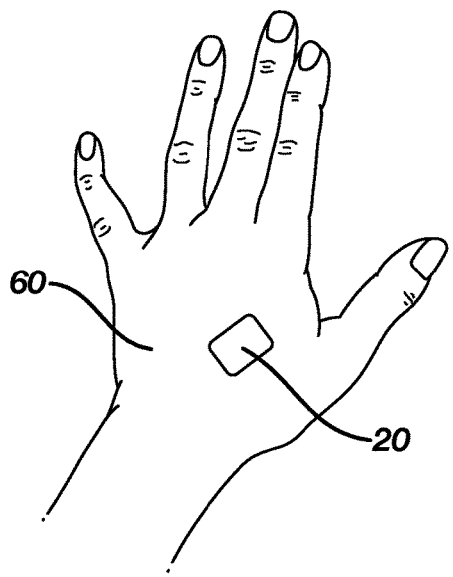
FIG. 8 illustrates a second step of wound dressing assembly use when the backing of the article is removed leaving a clear wound cover on the hand of the user.
Figure 9:
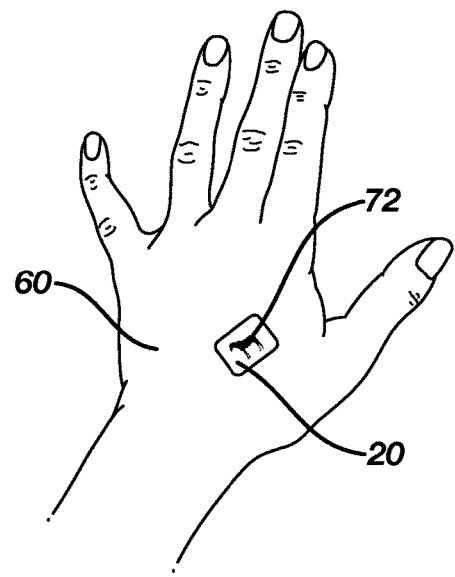
FIG. 9 illustrates an alternative second step of wound dressing assembly use when the backing of the article is removed leaving a decorated wound cover on the hand of the user.

FIGS. 7 to 9 are representations of methods of using the wound dressing assembly 10 of the present invention from a user's hand 60. FIG. 7 shows user's hand 60 on which is disposed wound dressing assembly 10. FIG. 8 shows wound cover 20 remaining on the user's hand 60 after removal of carrier 30. In this first embodiment, wound cover 20 is opaque to hide the wound from view. FIG. 9 shows a second embodiment wound cover 20, where a cartoon 72 is printed on second major surface 24 of wound cover 20. This embodiment also may hide the wound from view.

The process of manufacturing the wound dressing articles described above may be any of those conventionally known to produce adhesive bandages. The carrier and adhesive layers can be obtained by any methods available at present. For example, an extrusion process may be used for obtaining the carrier. In the same way, the adhesive layer can be made in any known manner. A carrier as described herein is obtained and an adhesive layer as described herein is applied to the first surface of the carrier. After adhesive layer is applied to the first surface of the, the wound-cover is associated with the adhesive layer, thus bonding the wound covering to the backing layer. Optionally, a release liner may be applied to the adhesive layer. The release liner is removed from the adhesive article prior to application by the user.

The wound dressing assembly 10 described above may also be ideally suited to deliver one or more active ingredients such as therapeutics to the surface of the skin. When contained in the assembly 10, one or more active ingredients may be contained primarily or exclusively in the wound cover 20 of assembly 10. Illustrative classes of active ingredients that may be delivered to the skin via wound dressing assembly 10 of the invention include, but are not limited to, antibiotics, analgesics, antipyretics, antimicrobials, antiseptics, antiallergics, anti-acne, anesthetics, anti-inflammatories, hemostats, cosmetics, vitamins, vasodilators, emollients, pH regulators, antipruritics, counterirritants, antihistamines and steroids. Specific active ingredients that may be delivered to the skin via the dressings of the invention include chlorhexidine, neomycin sulfate, polymyxin-B sulfate, zinc bacitracin, benzalkonium chloride, cetylpyridinium chloride, bupivacaine, tetracaine, cincaine, lidocaine, benzocaine, silver sulfadiazine, hydrocortisone, metandienone, trypsin, tolazoline, heparin, pramoxine, aloe vera, tretinoin, retinol, retinaldehyde, menthol, capsaicin, alpha hydroxy acids and vitamins such as Vitamin E.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:
1. A wound dressing assembly comprising:
    a. a wound cover having:
        i. a length and width substantially greater than a height;
        ii. a first major surface having disposed thereon a wound cover pressure sensitive adhesive comprising a colloidal absorbent and being arranged and configured to adhere to mammalian skin during use; and
        iii. a second major surface, opposite the first major surface wherein the second major surface of the wound cover is substantially impervious to bodily fluids; and
    b. a carrier having:
        i. a length and width substantially greater than a height;
        ii. a first major surface in facing relation and removably attached to the second major surface of the wound cover, the first major surface of the carrier having a first zone and a second zone at least partially surrounding the first zone, the first and second zones having disposed thereon at least one pressure sensitive adhesive arranged and configured to adhere to skin; and
        iii. a second major surface, opposite the first major surface of the carrier, wherein the first zone is larger in area than the second major surface of the wound cover, and further wherein, after application of the wound cover and carrier to skin for use, the carrier is removable from the wound cover to leave the wound cover adhered to the skin.

\* \* \* \* \*